United States Patent [19]

Sorensen et al.

[11] Patent Number: 5,436,252
[45] Date of Patent: Jul. 25, 1995

[54] 5-ARYL-3H-1,2,4-TRIAZOL-3-ONES AND THEIR USE IN THE TREATMENT OF NEURODEGENERATIVE DISORDERS

[75] Inventors: Stephen M. Sorensen; John M. Kane, both of Cincinnati; Francis P. Miller, Loveland, all of Ohio

[73] Assignee: Merrell Dow Pharmaceuticals Inc., Cincinnati, Ohio

[21] Appl. No.: 494,049

[22] Filed: Mar. 15, 1990

Related U.S. Application Data

[63] Continuation-in-part of Ser. No. 318,384, Mar. 3, 1989, abandoned, which is a continuation-in-part of Ser. No. 107,001, Oct. 16, 1987, abandoned, which is a continuation-in-part of Ser. No. 944,634, Dec. 19, 1986, abandoned.

[51] Int. Cl.$^6$ .............................. A61K 31/47
[52] U.S. Cl. ............................ 514/309; 514/314; 514/340; 514/384; 514/422; 514/444; 514/471; 514/464
[58] Field of Search ............... 514/384, 309, 314, 340, 514/422, 444, 471, 464

[56] References Cited

U.S. PATENT DOCUMENTS

| 3,514,466 | 5/1970 | Stahle et al. | 548/263.2 |
| 4,414,221 | 11/1983 | Parsons et al. | 514/384 |
| 4,946,856 | 8/1990 | Kane et al. | 514/384 |

FOREIGN PATENT DOCUMENTS

| 621842 | 2/1963 | Belgium | 548/263 |
| 894856 | 8/1983 | Belgium | 548/263 |
| 160447 | 8/1983 | German Dem. Rep. | 548/263 |
| 50-63119 | 5/1975 | Japan . | |
| 65-1537 | 3/1965 | South Africa . | |

OTHER PUBLICATIONS

Kane et al "2,4-dihydro-3H-1,2,4-triazole-3-thiones as potential antidepressants agents" CA 108-221674y (1988).

Deliwala et al "Further studies in substituted 4H-1,2,4-triazoles for possible hypoglycemic activity" CA 74-111968u (1971).

Mazzone et al "Cyclic derivatives from alkoxybenzohydrazides. Synthesis of pyrazoles, pyrroles and triazol-5-ones of pharmaceutical interest" CA 106-196338r (1987).

Akerblom et al "Nitrofuryltriazole derivatives as potential urinary tract antibacterial agents" CA 79-87327q (1973).

Kane et al "2,4-dihydro-3H-1,2,4-triazol-3-ones as anticonvulsant agents" CA 113-152341b (1990).

The Merck Manual "Convulsive Seizures (including epilepsy)" pp. 1008-1009 (1966).

G. Maffii, et al., Studio farmacologico di alcuni ossadiazoli e triazoli, *Farmaco 13*, 629-38 (1958). (Translation provided).

F. P. Miller, et al., FASEB J. 2, A1070, abstract 4501 (1988).

*Primary Examiner*—C. Warren Ivy
*Assistant Examiner*—A. A. Owens
*Attorney, Agent, or Firm*—Edlyn S. Simmons

[57] ABSTRACT

This invention relates to neuroprotective 5-aryl-3H-1,2,4-triazol-3-ones and to their use in the treatment of neurodegenerative disorders such as cerebral ischemia, stroke, Alzheimer's disease, Parkinson's disease, and Huntington's disease.

23 Claims, No Drawings

5-ARYL-3H-1,2,4-TRIAZOL-3-ONES AND THEIR USE IN THE TREATMENT OF NEURODEGENERATIVE DISORDERS

This is a continuation-in-part of application Ser. No. 318,384, filed Mar. 3, 1989, which is a continuation-in-part of application Ser. No. 107,001, filed Oct. 16, 1987, now abandoned, which is a continuation-in-part of application Ser. No. 944,634, filed Dec. 19, 1986, now abandoned.

BACKGROUND OF THE INVENTION

Degeneration of nerve cells in the brain is responsible for many disorders. Such disorders include Parkinson's disease, Huntington's disease, Alzheimer's disease, and the pathology associated with stroke and cerebral ischemia, and often include symptoms of tremor and spasticity. Excessive stimulation of receptors by the endogenous excitatory amino acids, glutamate and aspartate, is known to produce neuronal loss and to mimic many of the symptoms of these disorders. Similarly, administration of glutamate agonists such as quinolinic acid, kainic acid, and quisqualic acid to rodents has been shown to cause neuronal degeneration. The patterns of this loss have been compared to the neuronal loss accompanying neurodegenerative disorders such as Huntington's disease, parkinsonism and Alzheimer's disease in humans, suggesting that rapid and excessive release of endogenous glutamate, which acts as a toxin, is the common cause of the neurological symptoms arising from diverse disease processes, and indicating that antagonists of excitatory amino acids will be useful in the treatment of neurodegenerative disorders. Compounds such as MK-801, i.e., (S)-10,11-dihydro-5-methyl-5H-dibenzo(a,d)cyclohepten-5,10-imine, that have have been shown either to antagonize the seizures induced in mice by quinolinic acid, a compound thought to be an agonist at the N-methyl-D-aspartate (NMDA)-subtype of the glutamate receptor, or to antagonize hippocampal neurodegeneration after carotid artery occlusion in gerbils, are being developed for use as neuroprotectants.

SUMMARY OF THE INVENTION

More specifically this invention relates to compounds of the formula

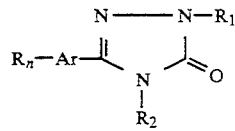

and the tautomers thereof, wherein
Ar represents phenyl, naphthyl or an aromatic heterocyclic moiety,
$R_1$ is hydrogen or $C_{1-4}$ lower alkyl,
$R_2$ is $C_{1-4}$ lower alkyl,
R is $C_{1-6}$ alkyl, $C_{1-6}$ alkoxy, hydroxy, halogeno, or trifluoromethyl, and n is zero, 1 or 2, or $R_n$-Ar is methylenedioxyphenyl,
and the pharmaceutically acceptable salts of the compounds wherein Ar is a nitrogen containing heterocyclic moiety.

DETAILED DESCRIPTION OF THE INVENTION

For R in the above general Formula I, halogeno preferably represents chloro or fluoro, and methyl and ethyl represent the preferred lower alkyl moieties, although all the straight, branched and cyclic manifestations thereof such as n-propyl, cyclopentyl, cyclohexyl and cyclopropyl are herein included. Lower alkoxy radicals include ethers having alkyl moieties paralleling the $C_{1-6}$ alkyl group. When n is 2, the R groups may be the same or different.

$R_1$ and $R_2$ are preferably methyl or ethyl, although any straight or branched $C_{1-4}$ lower alkyl group may be used. Compounds wherein $R_1$ is hydrogen are also preferred. The tautomeric forms are included for each of the compounds embraced within Formula I wherein $R_1$ is hydrogen.

When "Ar" is phenyl and n is one, representing a monosubstituted phenyl moiety, the R-substitutent may be located at the ortho, meta or para position, although the ortho- and para-substituted compounds are preferred. When Ar is disubstituted (i.e., n is 2), the 2,3-; 2,4-; 2,5-; 2,6-; 3,4-; and 3,5- positions may be substituted.

When "Ar" in formula I represents a heterocyclic moiety, such heterocyclic moieties as 2-, 3- or 4-pyridyl, 2- or 3-furyl, 2- or 3-thienyl, 2- or 3-pyrrolyl, N-($C_{1-4}$ alkyl)pyrrolyl, 6-isoquinolyl, 6-quinolyl and 3-quinolyl are contemplated. State of the art salts formed with nitrogen-containing heterocyclic moieties may be employed, with the hydrochloride being one of convenience and general applicability, such salts being formed by standard techniques well known in the art.

When "Ar" represents naphthyl, the 1- or 2-naphthyl isomer may be used, with the R moiety being attached thereto at any of the available positions.

The use of triazol-3-ones of formula I as anti-convulsants, especially for use in treatment of seizure disorders such as idiopathic epilepsy, is disclosed in copending application serial number 90,310.

As used herein, the term neurodegenerative disorders refers to diseases whose symptoms are caused by degeneration of nerve cells in the brain. A neurodegenerative disease is any disease that causes the loss of neurons in the brain, and specifically includes parkinsonism, Huntington's disease, Alzheimer's disease, and the tremor and spasticity resulting from stroke or cerebral ischemia. The objective of treatment of neurodegenerative diseases with the neuroprotective compounds of formula I is to prevent the loss of neurons and thereby slow or stop the development of symptoms in the patient or the worsening of symptoms already present.

Triazol-3-ones of formula I have been shown to antagonize the seizures induced in mice by quinolinic acid, an agonist at the N-methyl-D-aspartate (NMDA)-subtype of the glutamate receptor. In addition, triazol-3-ones of formula I have been shown to antagonize hippocampal neurodegeneration after carotid artery occlusion in gerbils. These results indicate that the active triazol-3-ones will have therapeutic utility in the treatment of neurodegenerative disorders such as stroke, cerebral ischemia, Huntington's disease, parkinsonism and Alzheimer's disease. Treatment of the neurodegenerative disorders with the compounds of Formula I will slow or halt the development of symptoms by preventing further loss of neurons.

To evaluate the compounds for their ability to antagonize the seizures induced in mice by quinolinic acid, mice were given an appropriate dose of the test compound and, at a selected time thereafter, quinolinic acid was given intracerebroventricularly (icv) at a dose of 7.7 μg dissolved in 5 μl of saline. This dose of quinolinic acid has been found to cause clonic-tonic seizures in 90–100% of otherwise untreated mice. Immediately following quinolinic acid administration, the animals were observed for 15 minutes. Table I shows either the $ED_{50}$ of the test compound or the number of test animals protected by a dose of 64 mg/kg of test compound.

the gerbil. This damage was assessed according to the scale below.

| | |
|---|---|
| 0 | No apparent damage |
| 1 | Damage at CA1/Subiculum Border and/or CA1/CA3 Border |
| 2 | Obvious CA1 damage, restricted to <50% of field |
| 3 | Damage to >50% of CA1 field |
| 4 | Damage extending beyond CA1 field |

Using the above criteria, the protective effect of 5-(4-chlorophenyl)-2,4-dihydro-4-ethyl-2-methyl-3H-1,2,4-triazol-3-one was compared with MK-801, a drug which is being developed for use as a neuroprotectant in

TABLE I

Antagonism of Quinolinic Acid Induced Seizures by Compounds of Formula I

| $R_n$—Ar | $R_1$ | $R_2$ | Mice Protected 64 mg/Kg IP | $ED_{50}$ IP mg/Kg | $ED_{50}$ PO mg/Kg |
|---|---|---|---|---|---|
| 4-ClC$_6$H$_4$ | CH$_3$ | CH$_3$ | 8/10 | | |
| 3-(n-C$_4$H$_9$O)—4-CH$_3$OC$_6$H$_3$ | H | CH$_3$ | 7/10 | | |
| 3-(n-C$_4$H$_9$O)—4-CH$_3$OC$_6$H$_3$ | CH$_3$ | CH$_3$ | 6/10 | | |
| 3-(cyclo-C$_5$H$_9$O)—4-CH$_3$OC$_6$H$_3$ | CH$_3$ | CH$_3$ | 6/10 | | |
| 2-ClC$_6$H$_4$ | CH$_3$ | CH$_3$ | 6/10 | | |
| 4-ClC$_6$H$_4$ | H | CH$_3$ | 6/10 | | |
| 2-ClC$_6$H$_4$ | H | CH$_3$ | 6/10 | 64.9 (30'); >64 (2 hr) | |
| 3,4-Cl$_2$C$_6$H$_3$ | H | CH$_3$ | 5/10 @ 32 (60') | <8 (30') | >16 |
| C$_6$H$_5$ | C$_2$H$_5$ | CH$_3$ | 5/10 | | |
| C$_6$H$_5$ | CH$_3$ | CH$_3$ | 5/10 | | |
| C$_6$H$_5$ | H | CH$_3$ | 5/10 | | |
| 4-Pyridyl | H | CH$_3$ | 3/10 | | |
| 3-(cyclo-C$_5$H$_9$O)—4-CH$_3$OC$_6$H$_3$ | H | CH$_3$ | 2/10 | | |
| 3,4-Cl$_2$C$_6$H$_3$ | CH$_3$ | CH$_3$ | | 32 > 64 | |
| 2-Thienyl | C$_2$H$_5$ | CH$_3$ | | <8–64 | |
| 4-ClC$_6$H$_4$ | CH$_3$ | C$_2$H$_5$ | | 25.9 (30') 17.2 (60)' 39.2 (2 hr) | 29.9 (30') 52.26 (4 hr) >128 (24 hr) |
| 4-ClC$_6$H$_4$ | H | C$_2$H$_5$ | | 51 (30') | |

Male mongolian gerbils (Tumblebrook Farms) weighing 45 to 60 gms were used for the experiments measuring hippocampal neurodegeneration after carotid artery occlusion. The gerbils were housed in small groups and allowed ad lib access to food and water prior to surgery. Following administration of drug, the gerbils were anesthetized with halothane (3.5%) and prepared for surgery.

An incision was made in the midline region of the neck and both carotid arteries were exposed and isolated from surrounding tissue. In sham operated animals the wounds were then closed and the animals were allowed to recover. In the hypoxic group the isolated carotid arteries were occluded for 5 minutes with 7 mm Mayfield aneurysm clips. Loss of blood flow to the cortex was confirmed by observation with an opthalmoscope of the blanching of the radial arteries in the retina of the ipsilateral eye. After 5 minutes the clips were removed and the gerbils were placed in their home cages and allowed to recover. After 7 days the gerbils were sacrificed by an overdose of chloral hydrate and perfused intracardially with 10 ml of 1% NaNO$_3$ followed by 15 ml of 10% buffered formalin. The brain was then removed and stored in buffered formalin for several days and then blocked for the hippocampus, sectioned at 12 micron intervals, and stained with cresyl violet. Damage to the CA1 region was assessed by 3 observers who were blind to the previous treatment of stroke. MK-801 at 5 mg/kg (30 minutes prior to ligation) reduced apparent damage by 28% in these experiments. 5-(4-Chlorophenyl)-2,4-dihydro-4-ethyl-2-methyl-3H-1,2,4-triazol-3-one at 40 mg/kg i.p. reduced damage by 66%.

The compounds of this invention will exert neuroprotective activity in the treatment of neurodegenerative disorders at oral dosage levels of about 0.25 to 40 mg/kg of body weight per day. Of course the degree of severity of the disease, age of the patient and other factors normally considered by the attending diagnostician will influence the individual regimen for each patient. In general, the parenterally administered doses are about ¼ to ½ that of the orally administered dose.

For oral administration the compounds can be formulated into solid or liquid preparations such as capsules, pills, tablets, troches, powders, solutions, suspensions or emulsions. Solid unit dosages can be in the form of a capsule which can be of the ordinary gelatin type containing, for example, lubricants and inert fillers such as lactose, sucrose or cornstarch. In another embodiment the compounds of general formula I can be tableted with conventional tablet bases such as lactose, sucrose and cornstarch, in combination with binders such as acacia, cornstarch or gelatin, disintegrating agents such as potato starch or alginic acid, and a lubricant such as stearic acid or magnesium stearate.

For parenteral administration, the compounds may be administered as injectable dosages of a solution or suspension of the compound in a physiologically acceptable diluent with a pharmaceutical carrier which can be a sterile liquid such as water, alcohol, oils and other acceptable organic solvents, with or without the addition of a surfactant and other pharmaceutically acceptable adjuvants. Illustrative of oils which can be employed in these preparations are those of petroleum, animal, vegetable or synthetic origin, for example, peanut oil, soybean oil and mineral oil. In general, water, saline, aqueous dextrose and related sugar solutions, ethanol, glycols such as propylene glycol or polyethylene glycol, or 2-pyrrolidone are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic ®, a silicone rubber manufactured by the Dow-Corning Corporation.

As is true for most classes of compounds generally suitable as therapeutic agents, certain subgeneric groups and specific members of that class, in the light of their overall biological profile, are preferred. The preferred Ar moiety is phenyl, with pyridyl and thienyl being the preferred heterocyclic aryl moieties. The preferred R substituent is chloro, with chloro at the 2- or 4-positions of the aromatic moiety being preferred. It is preferred that the $R_2$ alkyl substituent be methyl and ethyl, with hydrogen, and especially methyl or ethyl being the preferred groups for $R_1$. Particularly preferred compounds are:

5-(4-chlorophenyl)-2,4-dihydro-4-ethyl-2-methyl-3H-1,2,4-triazol-3-one,
5-(2-thienyl)-2,4-dihydro-2-ethyl-4-methyl-3H-1,2,4-triazol-3-one,
5-(4-chlorophenyl)-2,4-dihydro-2,4-dimethyl-3H-1,2,4-triazol-3-one,
5-[3-(n-butoxy)-4-methoxyphenyl]-2,4-dihydro-4-methyl-3H-1,2,4-triazol-3-one,
5-(3,4-dichlorophenyl)-2,4-dihydro-4-methyl-3H-1,2,4-triazol-3-one,
5-(3,4-dichlorophenyl)-2,4-dihydro-2,4-dimethyl-3H-1,2,4-triazol-3-one,
5-(4-chlorophenyl)-2,4-dihydro-4-ethyl-3H-1,2,4-triazol-3-one, and
5-(2-chlorophenyl)-2,4-dihydro-4-methyl-3H-1,2,4-triazol-3-one.

The compounds of Formula I may readily be prepared using processes and techniques analogously known in the art, for example in the method of S. Kuboda and M. Uda, Chem. Pharm. Bull. 21, 1342 (1979), as seen by the following reaction scheme:

$R_n$—ArCONHNH$_2$ + R$_2$NCO ⟶ $R_n$—ArCONHNHCONHR$_2$

II      III             IV

↓ Base

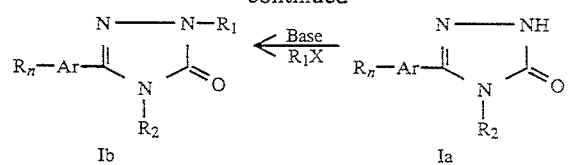

Ib                     Ia wherein R, Ar, n, $R_1$ and $R_2$ are as defined in formula I, and X is a suitable leaving group.

The preparation of the 1-aroylsemicarbazides (IV) is readily effected by reacting hydrazide (II) with an $R_2$-substituted isocyanate (III) by contacting the reactants together in a suitable aprotic solvent, preferably one in which the hydrazide reactant is soluble, e.g., tetrahydrofuran (THF), CHCl$_3$, CH$_2$Cl$_2$, benzene, toluene, Et$_2$O and the like. The reaction is quite rapid and may be carried out at 0° C. to about room temperature and, although the reaction proceeds rapidly, the mixture may be left for 24 hours without any significant decrease in yield. The required hydrazides and isocyanates are readily available but may be prepared by known techniques quite obvious to one of ordinary skill in the art.

The desired 5-aryl-2,4-dihydro-3H-1,2,4-triazol-3-ones (Ia) may be prepared by reacting the semicarbazides (IV) with a base, preferably an aqueous alkali metal hydroxide (e.g., NaOH, KOH) at about 50-°120° C., although reflux temperatures are preferred. Normal reaction time is about 8 ; hours, although 4–24 hours may be needed depending on the temperature of the mixture and the structure of the reactant.

The desired 2,4-disubstituted-2,4-dihydro-3H-1,2,4-triazol-3-ones (Ib) may be prepared by reacting the 4-substituted-2,4-dihydro-3H-1,2,4-triazol-3-ones (Ia) with an appropriate $R_1X$ reactant wherein X is a suitable leaving group, e.g., Cl, Br, OSO$_2$CF$_3$ and the like. Preferably the reaction takes place in a solution of an aqueous alkali metal hydroxide, (e.g., KOH, NaOH) although more reactive bases (e.g., NaH, KH, LDA) may be used if the reaction is affected under aprotic dry conditions. The reaction preferably takes place at room temperatures over periods of about 18 hours to two weeks.

The following specific examples are given to illustrate the preparation of the compounds of this invention.

Preparation of Intermediate 1-Aroyl-4-substituted Semicarbazides

EXAMPLE 1

1-(4-Chlorobenzoyl)-4-ethylsemicarbazide

A stirred suspension of 4-chlorobenzoic acid, hydrazide (17.1 g, 1.00×10$^{-1}$ mole), and THF (425 ml) was warmed until homogeneous, at which time ethyl isocyanate (8.7 ml, 1.1×10$^{-1}$ mole) was added via syringe. A precipitate soon formed. After stirring overnight the reaction was diluted with Et$_2$O and the precipitate was collected by filtration affording a colorless powder: 23.7 g (98%). Crystallization from ethanol gave a colorless solid: 21.4 g (88%), Mp 237°–239° C.

EXAMPLE 2

1-(4-Pyridoyl)-4-methylsemicarbazide

When, in the procedure of Example 1, isonicotinic acid hydrazide is substituted for 4-chlorobenzoic acid hydrazide and methyl isocyanate is substituted for ethyl isocyanate, the title compound is obtained.

EXAMPLE 3

1-(2-Thienoyl)-4-methylsemicarbazide

When in the procedure of Example 1, 2-thiophenecarboxylic acid hydrazide is substituted for 4-chlorobenzoic acid hydrazide and methyl isocyanate is substituted for ethyl isocyanate, the title compound is obtained.

Preparation of 5-Aryl-4-substituted-2,4-dihydro-3H -1,2,4-triazol-3-ones

EXAMPLE 4

5-(4-Chlorophenyl )2,4-dihydro-4-ethyl-3H-1,2,4-triazol-3-one

I-(4-Chlorobenzoyl)-4-ethylsemicarbazide (23.7 g, 9.81 ×10$^{-2}$ mole) and 1 molar aqueous NaOH (118 ml, 1.18×10$^{-1}$ mole) were stirred and warmed to reflux. After refluxing 23 hours, heating was discontinued and the reaction was acidified by the dropwise addition of 1 molar aqueous hydrochloric acid (130 ml, 1.30×10$^{-1}$ mole). A colorless solid formed as the reaction was acidified and, after cooling in an ice bath, this was collected by filtration. Crystallization from isopropanol gave colorless spars: 18.2 g (83%), Mp 188°–189° C.

EXAMPLE 5

2,4-Dihydro-4-methyl-5-(4-pyridinyl)-3H-1,2,4-triazol-3-one

When, in the procedure of Example 4, 1-(4-pyridoyl)-4-methylsemicarbazide is substituted for 1-(4-chlorobenzoyl)-4-ethylsemicarbazide, the title compound is obtained. Mp 249°–251° C.

EXAMPLE 6

5-(2-Thienyl)-2,4-dihydro-4-methyl-3H-1,2,4-triazol-3-one

When, in the procedure of Example 4, 1-(2-thienoyl)-4-methylsemicarbazide is substituted for 1-(4-chlorobenzoyl)-4-ethylsemicarbazide, the title compound is obtained. Mp 183°–185° C.

Preparation of 5-Aryl-2,4-dihydro-2,4-disubstituted-3H-1,2,4-triazol-3-ones

EXAMPLE 7

5-(4-Chlorophenyl)-2,4-dihydro-4-ethyl-2-methyl-3H-1,2,4-triazol-3-one

To a stirred, room temperature solution of 5-(4-chlorophenyl) -2,4-dihydro-4-ethyl-3H-1,2,4-triazol-3-one (6.00 g, 2.68×10-2 mole) and 1 molar aqueous NaOH (30.0 ml, 3.00×10$^{-2}$ mole) was added a solution of methyl iodide (2.5 ml, 4.0×10$^{-2}$ mole) and ethanol (10 ml). After stirring overnight at room temperature, the reaction mixture was transferred to a separatory funnel where it was extracted three times with EtOAc. The EtOAc extracts were combined, washed with saturated aqueous NaCl, and dried over Na$_2$SO$_4$. The drying agent was removed by filtration and the filtrate was evaporated at reduced pressure leaving an oil which slowly solidified. Chromatography and crystallization from cyclohexane gave small colorless needles: 3.4 g (53%), Mp 73°–75° C.

EXAMPLE 8

5-(2-Thienyl)-2,4-dihydro-2,4-dimethyl-3H-1,2,4-triazol-3-one

When, in the procedure of Example 7, 5-(2-thienyl)-2,4-dihydro -4-methyl-3H-1,2,4-triazol-3-one is substituted for 5-(4-chlorophenyl)-2,4-dihydro-4-ethyl-3H-1,2,4-triazol-3-one, the title compound is obtained. Mp 108°–110° C.

In a similar manner the following compounds also may be prepared.

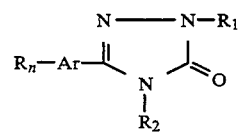

| R$_n$—Ar | R$^1$ | R$^2$ | Mp (°C.) |
|---|---|---|---|
| C$_6$H$_5$ | H | CH$_3$ | 177–178 |
| C$_6$H$_5$ | CH$_3$ | CH$_3$ | 140–141 |
| C$_6$H$_5$ | C$_2$H$_5$ | CH$_3$ | 87–89 |
| C$_6$H$_5$ | H | C$_2$H$_5$ | 163–165 |
| 2-ClC$_6$H$_4$ | H | CH$_3$ | 168–170 |
| 2-ClC$_6$H$_4$ | CH$_3$ | CH$_3$ | 61–63 |
| 4-ClC$_6$H$_4$ | H | CH$_3$ | 213–215 |
| 4-ClC$_6$H$_4$ | CH$_3$ | CH$_3$ | 126–128 |
| 4-ClC$_6$H$_4$ | C$_2$H$_5$ | CH$_3$ | 79–81 |
| 4-ClC$_6$H$_4$ | C$_2$H$_5$ | C$_2$H$_5$ | 62–64 |
| 4-ClC$_6$H$_4$ | n-C$_3$H$_7$ | C$_2$H$_5$ | oil |
| 2-FC$_6$H$_4$ | H | CH$_3$ | 189–191 |
| 2-FC$_6$H$_4$ | CH$_3$ | CH$_3$ | 69–71 |
| 4-FC$_6$H$_4$ | H | CH$_3$ | 216–218 |
| 4-FC$_6$H$_4$ | CH$_3$ | CH$_3$ | 104–106 |
| 3,4-Cl$_2$C$_6$H$_3$ | H | CH$_3$ | 170–172 |
| 3,4-Cl$_2$C$_6$H$_3$ | CH$_3$ | CH$_3$ | 107–109 |
| 4-CH$_3$C$_6$H$_4$ | H | CH$_3$ | 206–208 |
| 4-CH$_3$C$_6$H$_4$ | CH$_3$ | CH$_3$ | 92–94 |
| 4-CH$_3$O-3-(n-C$_4$H$_9$O)C$_6$H$_3$ | H | CH$_3$ | 96–98 |
| 4-CH$_3$O-3-(n-C$_4$H$_9$O)C$_6$H$_3$ | CH$_3$ | CH$_3$ | 112–114 |
| 4-CH$_3$O-3-(cyclo-C$_5$H$_9$O)C$_6$H$_3$ | H | CH$_3$ | 184–186 |
| 4-CH$_3$O-3-(cyclo-C$_5$H$_9$O)C$_6$H$_3$ | CH$_3$ | CH$_3$ | 153–155 |
| 2-Thienyl | C$_2$H$_5$ | CH$_3$ | 47–49 |

What is claimed is:

1. A method for the treatment of neurodegenerative disorders which comprises administering a neuroprotective amount of a compound of the formula

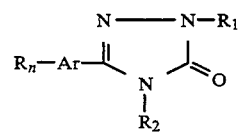

wherein Ar represents phenyl, naphthyl or an aromatic heterocyclic moiety selected from the group consisting of pyridyl, furyl, thienyl, pyrrolyl, N-(C$_{1-4}$ alkyl)pyrrolyl, isoquinolyl and quinolyl, R$_1$ is hydrogen or C$_{1-4}$ lower alkyl, R$_2$ is C$_{1-4}$ lower alkyl, R is C$_{1-6}$ alkyl, C$_{1-6}$ alkoxy, hydroxy, halogeno, or trifluoromethyl, and n is zero, 1 or 2, or R$_n$-Ar is methylenedioxyphenyl, or the pharmaceutically acceptable salt of a compound wherein Ar is a nitrogen-containing heterocyclic moiety.

2. A method of claim 1 wherein Ar is phenyl.

3. A method of claim 1 wherein R$_1$ is hydrogen, methyl or ethyl.

4. A method of claim 1 wherein R$_2$ is methyl or ethyl.

5. A method of claim 1 wherein Ar is phenyl and R is halogeno.

6. A method of claim 5 wherein R is chloro.

7. A method of claim 5 wherein the compound is 5-(4-chlorophenyl)-2,4-dihydro-4-ethyl-2-methyl-3H-1,2,4-triazol-3-one.

8. A method of claim 5 wherein the compound is 5-(4-chlorophenyl)-2,4-dihydro-2,4-dimethyl-3H-1,2,4-triazol-3-one.

9. A method of claim 5 wherein the compound is 5-(3,4-dichlorophenyl)-2,4-dihydro-4-methyl-3H-1,2,4-triazol-3-one.

10. A method of claim 5 wherein the compound is 5-(3,4-dichlorophenyl)-2,4-dihydro-2,4-dimethyl-3H-1,2,4-triazol-3-one.

11. A method of claim 5 wherein the compound is 5-(4-chlorophenyl)-2,4-dihydro-4-ethyl-3H-1,2,4-triazol-3-one.

12. A method of claim 5 wherein the compound is 5-(2-chlorophenyl)-2,4-dihydro-4-methyl-3H-1,2,4-triazol-3-one.

13. A method of claim 1 wherein Ar is phenyl and R is $C_{1-6}$ alkoxy.

14. A method of claim 13 wherein the compound is 5-[3-(n-butoxy)-4-methoxyphenyl]-2,4-dihydro-4-methyl-3H-1,2,4-triazol-3-one.

15. A method of claim 1 wherein Ar is an aromatic heterocyclic moiety.

16. A method of claim 15 wherein Ar is 2- or 3-thienyl.

17. A method of claim 16 wherein the compound is 5-(2-thienyl)-2,4-dihydro-2-ethyl-4-methyl-3H-1,2,4-triazol-3-one.

18. A method of claim 15 wherein Ar is 2-, 3- or 4-pyridyl.

19. A method of claim 1 for the treatment of stroke.

20. A method of claim 1 for the treatment of cerebral ischemia.

21. A method of claim 1 for the treatment of parkinsonism.

22. A method of claim 1 for the treatment of Alzheimer's disease.

23. A method of claim 1 for the treatment of Huntington's disease.

* * * * *